(12) United States Patent
Tran

(10) Patent No.: US 12,243,647 B2
(45) Date of Patent: Mar. 4, 2025

(54) SYSTEMS AND METHODS FOR ESTIMATING EMBRYO VIABILITY

(71) Applicant: Vitrolife A/S, Viby (DK)

(72) Inventor: Dang-Dinh-Ang Tran, Zetland (AU)

(73) Assignee: Vitrolife A/S, Viby (DK)

( * ) Notice: Subject to any disclaimer, the term of this patent is extended or adjusted under 35 U.S.C. 154(b) by 459 days.

(21) Appl. No.: 16/772,676

(22) PCT Filed: Dec. 14, 2018

(86) PCT No.: PCT/AU2018/051335
§ 371 (c)(1),
(2) Date: Jun. 12, 2020

(87) PCT Pub. No.: WO2019/113643
PCT Pub. Date: Jun. 20, 2019

(65) Prior Publication Data
US 2020/0311916 A1    Oct. 1, 2020

(30) Foreign Application Priority Data

Dec. 15, 2017 (AU) ............................... 2017905017
May 18, 2018 (AU) ............................... 2018901754

(51) Int. Cl.
*G06K 9/00* (2022.01)
*A61B 5/00* (2006.01)
(Continued)

(52) U.S. Cl.
CPC ........... *G16H 50/30* (2018.01); *A61B 5/4362* (2013.01); *A61B 5/7267* (2013.01);
(Continued)

(58) Field of Classification Search
None
See application file for complete search history.

(56) References Cited

U.S. PATENT DOCUMENTS 9,177,192 B2    11/2015  Wang et al.
9,934,364 B1 *   4/2018  Kumar ................... G16B 25/10
(Continued)

FOREIGN PATENT DOCUMENTS

CN          105408746 A        3/2016
WO         2014/089647         6/2014
(Continued)

OTHER PUBLICATIONS

Khan Aisha et al, "Deep Convolutional Neural Networks for Human Embryonic Cell Counting", Computer Vision—ECCV 2016 Workshops, Cham, doi:10.1007/978-3-319-46604-0, ISBN 978-3-319-46604-0, (Oct. 8, 2016), URL: https://link.springer.com/content/pdf/10.1007/978-3-319-46604-0_25.pdf, (Jun. 3, 2021), XP055810280.
(Continued)

*Primary Examiner* — Wei Wen Yang
(74) *Attorney, Agent, or Firm* — Honigman LLP

(57) ABSTRACT

A computer-implemented method, including the steps of: receiving video data of a human embryo, the video data representing a sequence of images of the human embryo in chronological order; applying at least one three-dimensional (3D) artificial neural network (ANN) to the video data to determine a viability score for the human embryo, wherein the viability score represents a likelihood that the human embryo will result in a viable embryo or a viable fetus; and outputting the viability score.

20 Claims, 17 Drawing Sheets

(51) Int. Cl.
| | |
|---|---|
| G06T 7/00 | (2017.01) |
| G06T 11/60 | (2006.01) |
| G06V 10/82 | (2022.01) |
| G06V 20/69 | (2022.01) |
| G16H 30/40 | (2018.01) |
| G16H 50/20 | (2018.01) |
| G16H 50/30 | (2018.01) |
| G06V 10/44 | (2022.01) |

(52) U.S. Cl.
CPC .......... *A61B 5/7275* (2013.01); *G06T 7/0012* (2013.01); *G06T 11/60* (2013.01); *G06V 10/82* (2022.01); *G06V 20/698* (2022.01); *G16H 30/40* (2018.01); *G16H 50/20* (2018.01); *G06T 2207/10016* (2013.01); *G06T 2207/20076* (2013.01); *G06T 2207/20081* (2013.01); *G06T 2207/20084* (2013.01); *G06T 2207/30044* (2013.01); *G06V 10/454* (2022.01)

(56) References Cited

U.S. PATENT DOCUMENTS

| | | | |
|---|---|---|---|
| 2014/0017717 A1 | 1/2014 | Loewke et al. | |
| 2014/0247972 A1* | 9/2014 | Wang | G06K 9/6277 |
| | | | 382/133 |
| 2020/0226750 A1* | 7/2020 | Shafiee | G06T 7/0012 |

FOREIGN PATENT DOCUMENTS

| | | | | |
|---|---|---|---|---|
| WO | 2014/134550 A1 | 9/2014 | | |
| WO | 2015/069824 A2 | 5/2015 | | |
| WO | 2017/027475 A1 | 2/2017 | | |
| WO | WO-2018179769 A1 * | 10/2018 | ......... | G06K 9/00127 |
| WO | 2019/082713 A1 | 5/2019 | | |

OTHER PUBLICATIONS

Carreira Joao et al, "Quo Vadis, Action Recognition? A New Model and the Kinetics Dataset", 2017 IEEE Conference on Computer Vision and Pattern Recognition (CVPR), IEEE Computer Society, US, doi:10.1109/CVPR.2017.502, ISSN 1063-6919, (Jul. 21, 2017), pp. 4724-4733, (Nov. 6, 2017), XP033249828.

Baccouche, M. et al. "Sequential Deep Learning for Human Action Recognition." In International workshop on human behavior understanding, 2011, pp. 29-39.

Ji, S. et al. "3D Convolutional Neural Networks for Human Action Recognition," IEEE transactions on pattern analysis and machine intelligence, 2012, vol. 35 (1), pp. 221-231.

Office Action issued on Jun. 18, 2021 in Australian Patent Application No. 2018384082.

Extended European Search Report Issued on Jun. 14, 2021 in European Patent Application No. 18 889 137.8.

International Search Report and Written Opinion for PCT/AU2018/051335 mailed Mar. 13, 2019.

Kheradmand, S. "Human embryo component detection using computer vision." Thesis, Applied Sciences: School of Engineering Science, Apr. 2017, pp. i-xii, 1-77.

Kheradmand, S. et al. "Inner Cell Mass Segemntation in Human HMC Embryo Images Using Fully Convolutional Network," IEEE International Conference on Image Processing (ICIP) 2017 (Sep. 17, 2017) pp. 1752-1756.

Khan, A. "Automated Monitoring of Early Stage Human Embryonic Cells in Time-lapse Microscopy Images." Doctor of Philosophy Thesis, The Australian National University, 2016, pp. vii-xix, 1-123.

Singh, A. et al. "Automatic Segmentation of Trophectoderm in Microscopic Images of Human Blastocysts," IEEE Transactions on Bio-Medical Engineering, 2015, vol. 62(1), pp. 382-393.

"A 3D Neural Model for Video Analysis, Neural Nets WIRN09—Proceedings of the 19th Italian Workshop on Neural Nets", Vietri sul Mare, Salerno, Italy, May 28-30, 2009, Abstract.

"Human embryo component detection using computer vision." Thesis, Simon Fraser University, Applied Sciences: School of Engineering Science pp. i-xii, 1-77.

Inner Cell Mass Segemntation in Human HMC Embryo Images Using Fully Convolutional Network, IEEE International Conference on Image Processing (ICIP) pp. 1752-1756.

Automated Monitoring of Early Stage Human Embryonic Cells in Time-lapse Microscopy Images. Doctor of Philosophy Thesis, The Australian National University pp. vii-xix, 1-123.

Automatic Segmentation of Trophectoderm in Microscopic Images of Human Blastocysts, IEEE Transactions on Bio-Medical Engineering vol. 62(1), pp. 382-393.

English translation of Office Action issued in Israeli application No. 275253.

Nie, Weizhi et al. "3D Convolutional Networks-Based Mitotic Event Detection in Time-Lapse Phase Contrast Microscopy Image Sequences of Stem Cell Populations." 2016 IEEE Conference on Computer Vision and Pattern Recognition Workshops (CVPRW) (2016): 1359-1366.

\* cited by examiner

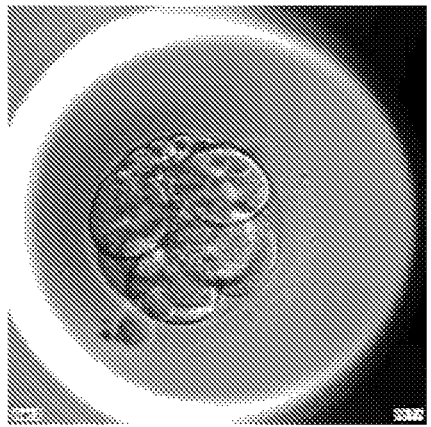 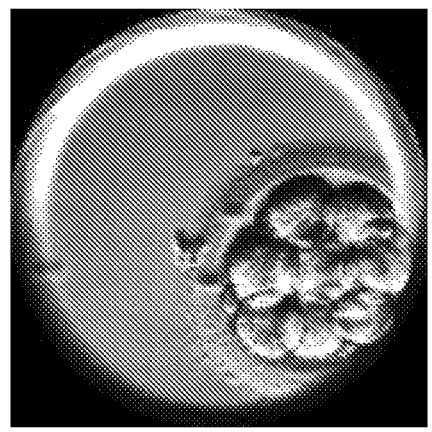
Figure 17A  Figure 17B
Figure 18

FIG. 19

SYSTEMS AND METHODS FOR ESTIMATING EMBRYO VIABILITY

RELATED APPLICATIONS

[1] This is an application claims the benefit under 35 USC 371 to International Application No. PCT/AU2018/051335, filed 14 Dec. 2018, which claims priority to Australian Provisional Patent Application Nos. 2017905017 entitled "Systems and methods for determining embryo viability" filed on 15 Dec. 2017, and 2018901754 entitled "Systems and methods for estimating embryo viability" filed on 18 May 2018. Each of these related applications are incorporated herein by reference and made a part of this application.

TECHNICAL FIELD

The present disclosure relates to systems and methods for estimating human embryo viability.

BACKGROUND

In vitro fertilisation (IVF) refers to processes/techniques where a woman's eggs are fertilised outside of the body. IVF typically involves administering fertility drugs to women to stimulate the maturation of multiple follicles as opposed to a single follicle in the normal cycle. These eggs are then retrieved surgically and transported to a laboratory where they are fertilised with the male partner's sperm or donated sperm. The fertilised eggs are then allowed to mature as embryos in a specialised culture environment, typically within an incubator. During this time, microscopic images of the developing embryos can be acquired using imaging technology within the incubator (such as an Embryoscope® incubator) to produce continuous time-lapse videos of the developing embryos.

Traditionally, multiple embryos are implanted to the woman's uterus to increase the overall success rate. The disadvantage of this approach is the increase in the probability of multiple pregnancies, which are associated with a higher risk of antenatal complications. As a result, one goal for improvement of IVF is to be able to perform a single embryo transfer for each pregnancy. The term "transfer" refers to a step in the process of assisted reproduction in which embryos are placed into the uterus of a female with the intent to establish a pregnancy.

To achieve this, one must be able to select a single embryo out of multiple developed embryos in accordance with highest pregnancy potential. This selection process is currently performed by embryologists who manually grade each embryo based on its appearance and the timing of critical developmental checkpoints.

Currently, the quality of each embryo is determined using a number of grading schemes. These schemes involve manual annotation of each embryo image or time-lapse video. Features that are considered in these grading systems include the morphological appearance of embryo as well as the precise timing of key developmental checkpoints. Currently, all solutions are purely workflow tools for embryologists. They depend entirely on the subjective judgement of the embryologist annotating each embryo. Some commonly used grading systems are the Gardner Blastocyst Grading System (https://www.advancedfertility.com/blastocystimages.htm) and KIDScore (http://www.vitrolife.com/sv/Products/EmbryoScope-Time-Lapse-System/KIDScore-decision-support-tool-/).

However, the selection process is an inexact science and is highly variable depending on each embryologist. Embryologists are required to make subjective judgements about the exact timing of certain developmental checkpoints as well as symmetry, size and uniformity. This is highly dependent on the operator's experience and personal opinion. This means embryologists often disagree with other embryologists or even themselves (when shown the same embryo again) on which embryo has the highest potential for transfer. As such, there is poor reproducibility and high inter- and intra-reader variability amongst embryologists. It is a time-consuming and labour-intensive process to label each time-lapse video. Manual embryo grading typically requires up to 1 hour per patient. It is unclear which features or which combination of features are ultimately predictive towards the pregnancy potential of each embryo. Current grading methods typically only analyse 2 to 4 isolated time frames that have been shown to independently result in a higher pregnancy rate. Furthermore, current systems, like the Embryoscope®, allow variable selection/deselection of multiple annotation/analysis parameters which may discourage analysis of how these aspects interact.

It is desired to address or ameliorate one or more disadvantages or limitations associated with the prior art, or to at least provide a useful alternative.

SUMMARY

Provided herein is a computer-implemented method, including the steps of:
  receiving video data of a human embryo, the video data representing a sequence of images of the human embryo in chronological order;
  applying at least one three-dimensional (3D) artificial neural network (ANN) to the video data to determine a viability score for the human embryo, wherein the viability score represents a likelihood that the human embryo will result in a viable embryo or a viable fetus; and
  outputting the viability score.

Provided herein is a system, including at least one processor configured to:
  receive video data of a human embryo, the video data including a sequence of images of the human embryo in chronological order;
  apply at least one three-dimensional (3D) artificial neural network to the video data to determine a viability score for the human embryo, wherein the viability score represents a likelihood that the human embryo will result in a viable embryo or a viable fetus; and
  output the viability score.

Provided herein is a method including:
  generating a viability score for a human embryo by probabilistically classifying data representing a video of the human embryo with an artificial neural network (ANN); or
  training an artificial neural network (ANN) to probabilistically classify data representing a video of a human embryo to generate a viability score for the human embryo.

Provided herein is a system, including at least one processor configured to:
  generate a viability score for a human embryo by probabilistically classifying data representing a video of the human embryo with an artificial neural network (ANN); or train an artificial neural network (ANN) to probabilistically classify data representing a video of a human embryo to generate a viability score for the human embryo.

BRIEF DESCRIPTION OF THE DRAWINGS

Some embodiments of the present invention are hereinafter described, by way of example only, with reference to the accompanying drawings, wherein:

FIGS. 17A and 17B show an example of images at slightly different points in time in a time-lapse embryo video before and after pre-processing, respectively;

FIG. 18 shows a division of the dataset when ensembling multiple neural networks; and FIG. 19 shows an exemplary user interface of the software package that displays the viability score.

DETAILED DESCRIPTION

Figure 1:
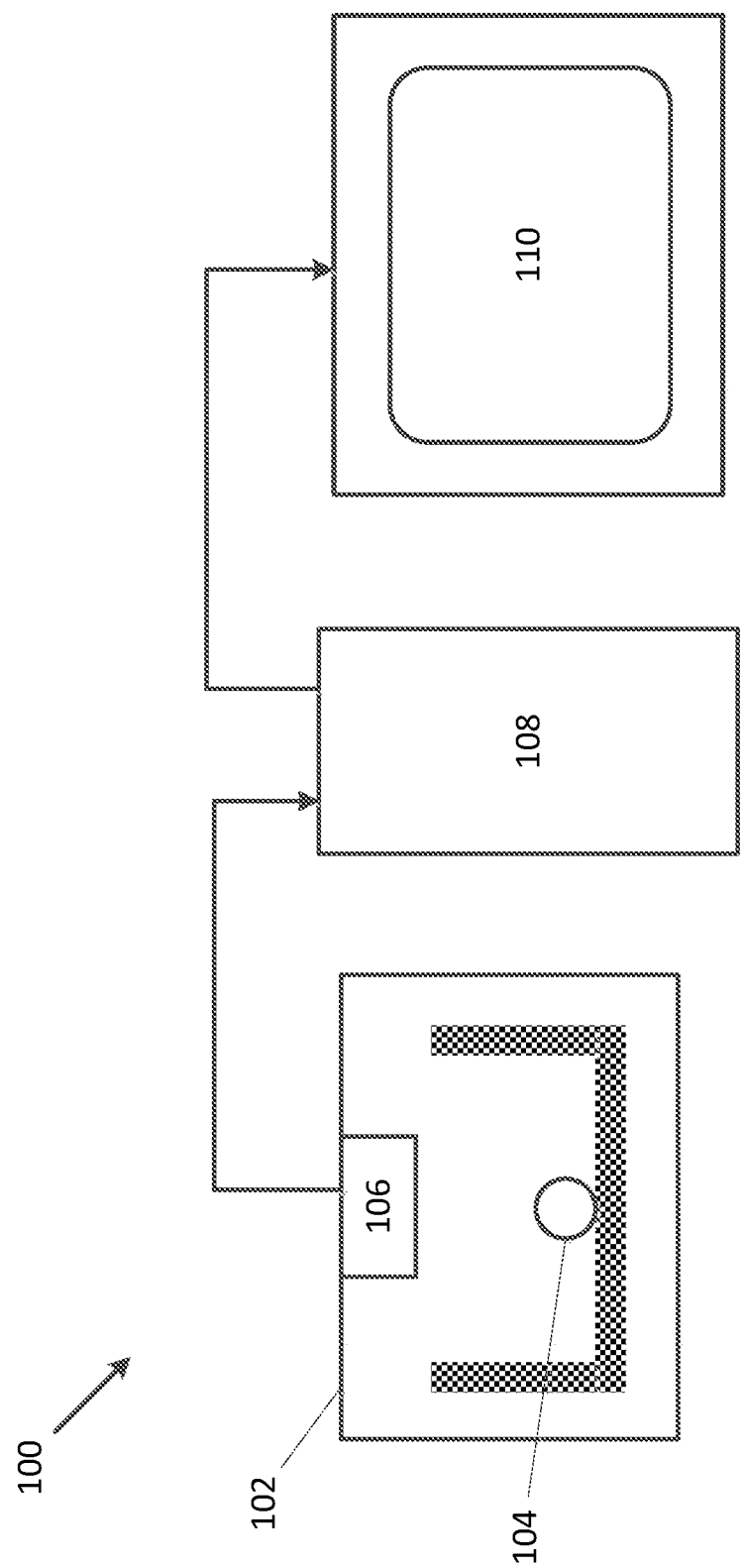
FIG. 1 shows a general structure of an exemplary system for estimating embryo viability.

Embodiments of the present invention provide a processing system for estimating embryo viability. The system is configured to receive video data of a human embryo and process the received video data to determine a viability score for the embryo. The video data includes a sequence of images in chronological order, so it is also referred to as "time-lapse video data".

It will be appreciated that the term "embryo" is intended to include the zygote or fertilized ovum, as well as the embryo that develops therefrom.

Generally, the viability score is or includes a probability, providing a prediction of the likelihood of an embryo leading to a successful pregnancy after implantation in the uterus. The embryo with a higher score has a higher probability of resulting in a viable embryo or a viable human fetus.

The viability scores may be used for determining, among multiple embryos incubated for a patient, a single embryo to be transferred into the uterus of a female. For example, the embryo with a higher score may be selected to be implanted in the uterus. This may prevent the risk of antenatal complications associated with multiple pregnancies due to transferring multiple embryos. Determining the embryo with the highest probability of resulting in a viable embryo or a viable fetus also decreases the time to pregnancy as the best embryo is transferred first, avoiding a failed transfer that necessitates a subsequent embryo transfer.

Alternatively, when multiple embryos are to be transferred (during subsequent treatment cycle using frozen embryos), the viability score may be used to decide the order in which embryos will be transferred into the uterus of a patient.

Some existing embryo assessment methods or grading systems (e.g., Gardner Blastocyst Grading System and KIDScore) may classify an embryo into a limited number of grades, e.g., a grade between 1 to 5.

By contrast, the present disclosure provides classification with a finer grain by estimating the probability of the embryo resulting in a viable embryo or a viable fetus. The classification methods used in the present disclosure may also be referred to as "probabilistically classifying" methods. This probabilistic classification provides a probability value, e.g., a percentage for each embryo, thus identifying finer differences between embryos. Accordingly, even embryos with the same grade according to existing grading systems can be ranked by the viability score. This allows for automatic generation of a ranking of a plurality of embryos based on their viability, and automatic selection of a single embryo for transfer from the plurality of embryos based on the ranking.

A viable embryo may be defined as an embryo having:
 a biochemical pregnancy detected based on a urine test or a blood test (e.g., for β-HCG); or
 a clinical pregnancy with a viable gestational sac or a viable yolk sac detected on ultrasound at a predetermined time (e.g., between 6-7 weeks) after embryo transfer.

A viable fetus may be defined as having:
 a viable fetal heart detected on maternal ultrasound a selected time (e.g., 6 or more weeks) following the embryo transfer; or
 a live birth at the end of the pregnancy.

Compared to some known measurements of embryo quality, e.g., embryo grade determined subjectively by an embryologist using existing grading schemes based on "how good the embryo looks", or implantation potential that represents the likelihood that the mother will have a positive pregnancy test following the embryo transfer, using the ultrasound fetal heart detection result 6 weeks following the embryo transfer provides a more objective and more reliable estimation of the viability of the embryo.

It will also be appreciated that the term "processing system" may refer to any electronic processing device or system, or computing device or system, or combination thereof (e.g., computers, web servers, smart phones, laptops, microcontrollers, etc.). The processing system may also be a distributed system. In general, processing/computing systems may include one more processors (e.g., CPUs, GPUs), memory componentry, and an input/output interface connected by at least one bus. They may further include input/output devices (e.g., keyboard, displays etc.). It will also be appreciated that processing/computing systems are typically configured to execute instructions and process data stored in memory (i.e., are programmable via software to perform operations on data).

FIG. 1 illustrates a general structure of an exemplary system 100 for estimating embryo viability. The system 100 is an example of the processing system.

As shown, the system 100 includes an incubator 102 for containing an embryo 104 and maintaining environmental conditions suitable for the embryo 104 to live. The incubator 102 includes an image sensor 106 for capturing time-lapse video data of the embryo 104.

The time-lapse video data captured by the image sensor 106 is sent to a processor 108 which applies a deep learning model to the time-lapse video data to determine a viability score for the embryo 104.

The viability score determined by the processor 108 may be subsequently output to a display 110 or other suitable output device for use by human staff, such as an embryologist.

It will be appreciated that no manual feature extraction or human annotation of the video data is required, and that the deep learning model is an end-to-end model receiving nothing but the raw video data to output the viability score.

In order to determine the viability score, the deep learning model is applied to the time-lapse video data. The deep learning module includes at least a three-dimensional (3D) artificial neural network (ANN), such as a 3D convolutional neural network (3D CNN).

A 3D CNN extracts features from both the spatial and the temporal dimensions by performing 3D convolutions, thereby capturing not only information contained in each single image frame in the video but also the motion information contained in multiple chronologically separated image frames, including adjacent image frames.

This is in contrast to analysing embryo quality by applying a machine learning model to only static images of the embryo, which takes into account only the information contained in each static image.

This is also in contrast to systems where humans are required to extract features such as morphological grading manually, or to annotate the exact timing of developmental milestones. Such systems may apply machine learning, but only to these extracted features and/or annotations, and to predict only the embryo grading. Accordingly, analysis of embryo time-lapse video using such systems may rely on the experience of the embryologist who manually or semi-automatically annotates features (e.g., morphological grading) or extracts timing of key developmental milestones. This process may be time-consuming and inaccurate. For example, each patient may have up to 30-20 embryos per treatment cycle, and each embryo may take up to 5 minutes to fully annotate. Accordingly, this is not a scalable solution for analysing a large number of time-lapse videos of embryos. By contrast, a fully end-to-end method for analysing time-lapse embryo videos using a 3D ANN may analyse, e.g., 10 embryos per second on a typical laptop, which is more efficient than the existing methods, and thus can make time-lapse video analysis of embryos scalable.

The system described herein extracts not only intra-frame features but also inter-frame features of the time-lapse video data, therefore capturing both the spatial and temporal features of the embryo. In this way, the described system may provide more comprehensive and more accurate analysis of the viability of an embryo compared to the existing methods.

Figure 2:
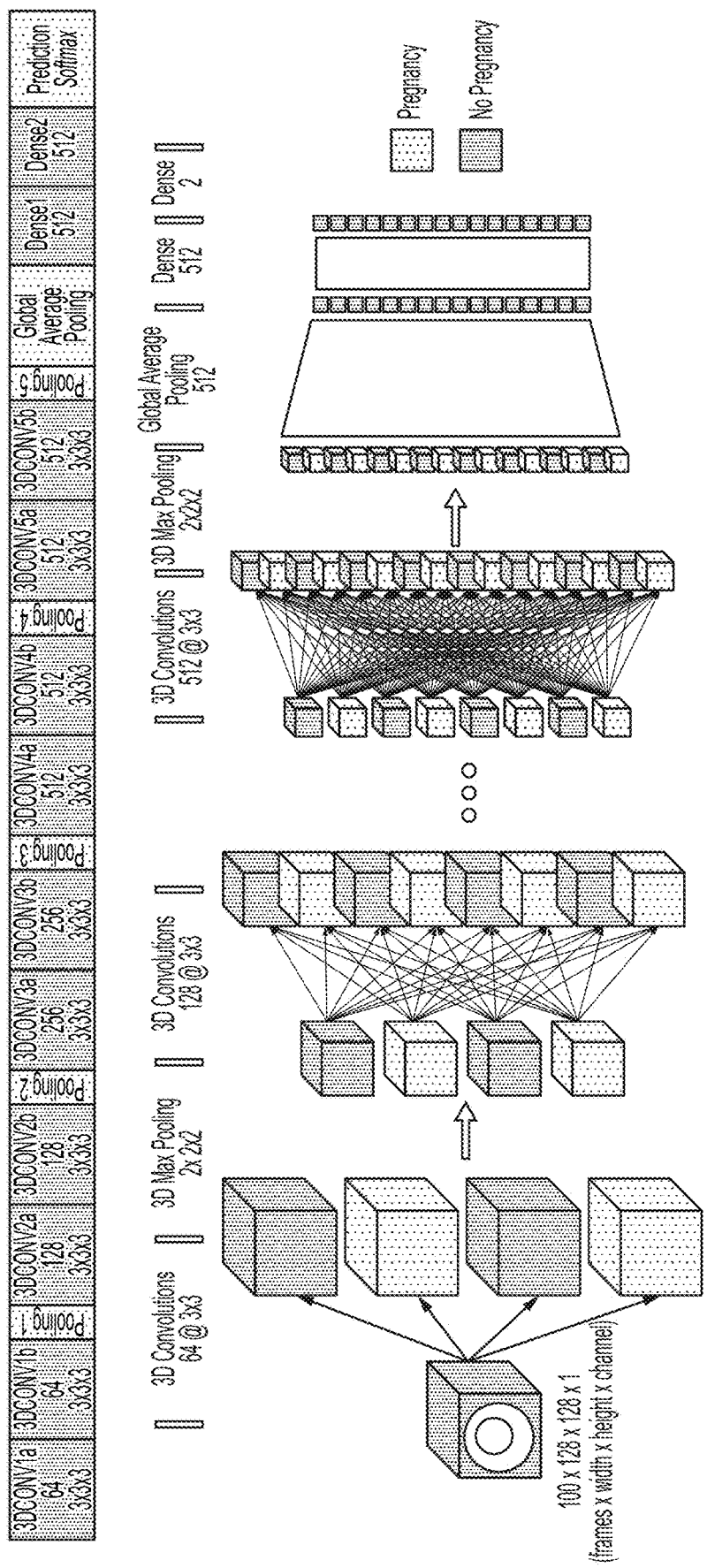
FIG. 2 shows an exemplary architecture of a 3D convolutional neural network used in one example.

FIG. 2 illustrates an exemplary architecture of the 3D CNN. In this example, the 3D CNN contains a series of convolution and pooling layers. More specifically, the CNN includes the repeated application of two 3×3×3 convolutions followed by a pooling operation. The last layer of the 3D CNN is a prediction layer which outputs the viability score.

Figure 3A:
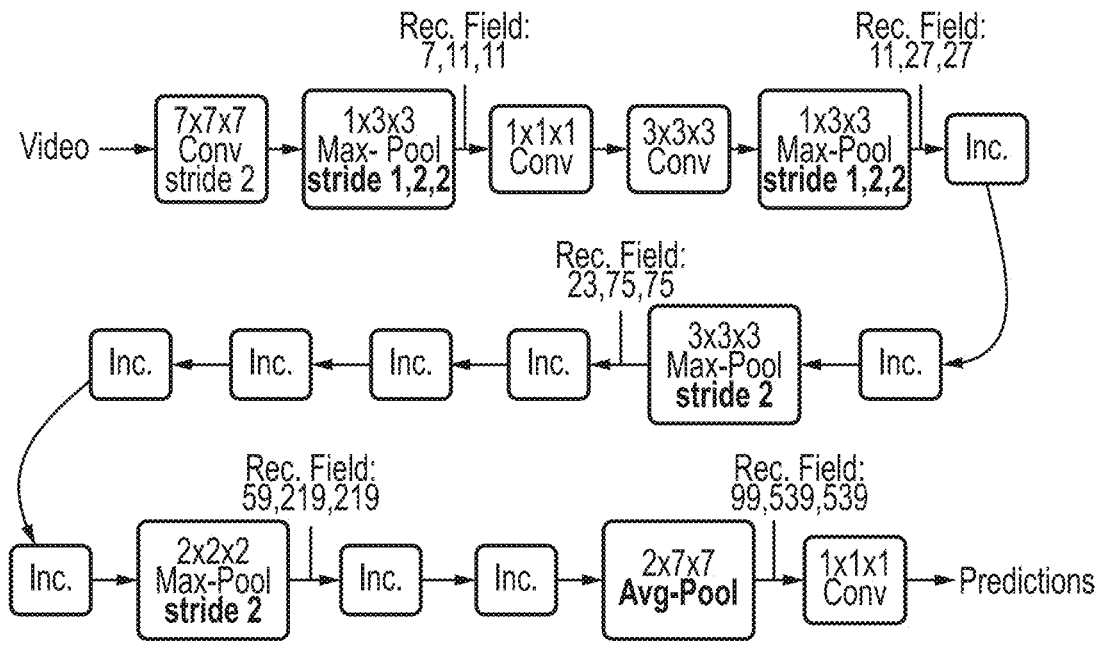
FIGS. 3A and 3B show an exemplary architecture of a 3D convolutional neural network schematic used in another example.
Figure 3B:
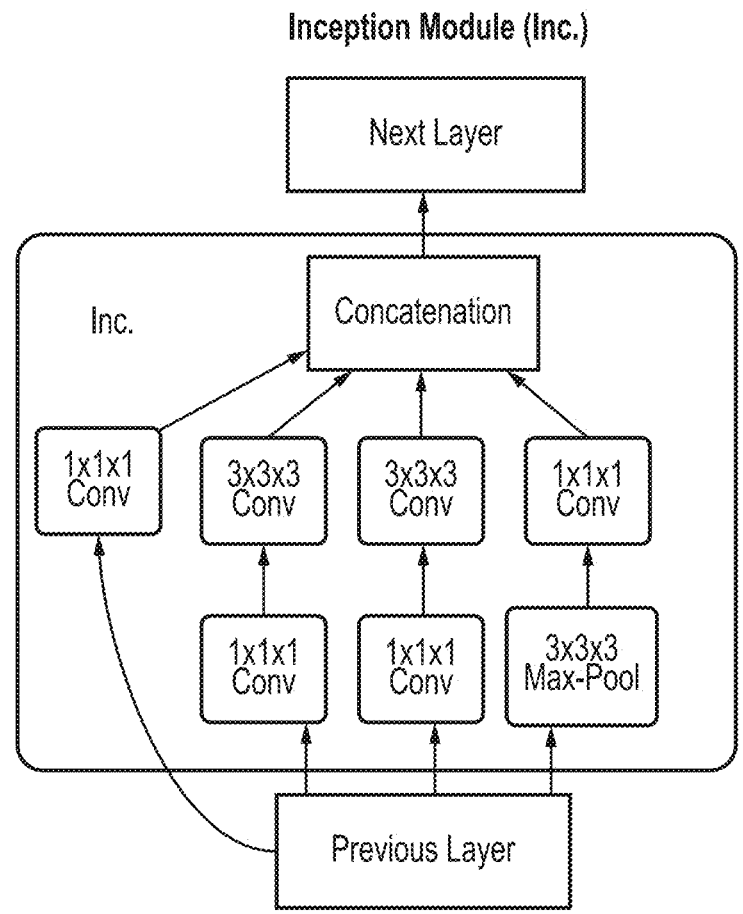

FIGS. 3A and 3B illustrate another exemplary architecture of the 3D CNN. In this example, the 3D CNN is an existing inflated 3D CNN, generated by inflating the two-dimensional (2D) filters and pooling kernels of a 2D CNN into 3D, as described in J Carreira, A Zisserman (2017), Quo vadis, action recognition? a new model and the kinetics dataset, 2017 IEEE *Conference on Computer Vision and Pattern Recognition (CVPR)*, 4724-4733. Accordingly, an N×N filter becomes an N×N×N filter after the inflation. As shown in FIG. 3A, the inflated 3D CNN has a plurality of convolution and polling layers, and a plurality of inception modules ("Inc."). FIG. 3B illustrates the architecture of the inception module.

The last layer of the 3D CNN shown in FIG. 3A is a linear classification layer, which outputs the viability score of the embryo.

As shown in FIG. 2 and FIGS. 3A and 3B, both exemplary architectures of the 3D CNN utilises 3D convolution kernels and pooling kernels, which allow the 3D CNN to capture spatio-temporal features of the embryo from the time-lapse video data.

It will be appreciated that the video data of the embryo may be derived from variety or formats, such as, for example, a sequence of still images in chronological order; or a time-lapse video document. In one example, the time-lapse video data is a time-lapse video document including 720 time-lapse image frames.

The 3D CNN is trained by using:
video data representing a plurality of sequences of images of a plurality of human embryos; and
pregnancy outcome data that indicates whether each of the plurality of human embryos has resulted in a viable embryo or a viable foetus.

As described hereinbefore, a viable embryo may be defined as an embryo having:
a biochemical pregnancy detected based on a urine test or a blood test (e.g., for β-HCG); or
a clinical pregnancy with a viable gestational sac or a viable yolk sac detected on ultrasound at a predetermined time (e.g., between 6-7 weeks) after embryo transfer.

A viable fetus may be defined as having:
a viable fetal heart detected on maternal ultrasound a selected time (e.g., 6 weeks, 7 weeks, 8 weeks, 9 weeks, 10 weeks, 11 weeks, 12 weeks, 3 months, 4 months, 5 months, 6 months, 8 months, 9 months) following the embryo transfer; or
a live birth at the end of the pregnancy.

Some existing machine-learning-based embryo assessment methods may require pre-analysis to manually determine which features of the embryo (e.g., blastomere symmetry, cytoplasmic appearance, and/or amount of fragmentation) to extract and analyse, or human annotation of key events (e.g., neural neurogenesis, musculoskeletal somitogenesis, and/or heart cardiogenesis) in the development of the embryo. By contrast, the 3D CNN described herein can be trained and used without manual selection or extraction of embryo characteristics/features, or human annotation of key development events. In other words, the deep learning model described herein provides an end-to-end embryo assessing process. This may be advantageous because medical professionals currently do not have a complete understanding in relation to what characteristics/features are the most useful characteristics/features in assessing the quality of a human embryo. Therefore, by providing an end-to-end embryo assessment process, the deep learning model described herein allows the system to learn and automatically determine which characteristics/features should be used, and thus can provide more accurate results than existing embryo assessment methods and systems. Furthermore pre-analysis to extract features such as symmetry, number of cells, degree of fragmentation and exact timing of key events is a subjective and non-repeatable process, and is highly variable between embryologists. A deep learning model applied to these data would be subjected to the same bottleneck in terms of performance.

The 3D CNN may be trained on one or more devices different from the processor 108. For example, 3D CNN may be trained by using a device including one or more graphical processing units (GPUs) and/or one or more central processing units (CPU).

Referring back to FIG. 1, in some embodiments, the processor 108 may pre-process the time-lapse video data before applying or training the deep learning module.

For example, the processor 108 may standardise the received time-lapse video data so that all videos span a predetermined time period.

The processor 108 may also perform a cropping step to retain predetermined areas in the time-lapse video data, e.g., areas that includes the embryo.

The processor 108 may further adjust contrast of the images in the time-lapse video data to enhance the video quality, for example by applying a contrast limited adaptive histogram equalisation (CLAHE).

Finally, the processor may resize the images in the time-lapse video data to a predetermined image size.

In some forms, the system 100 is further configured to produce a visual overlay for display over at least some images of the time-lapse video data. The visual overlay is indicative of the contribution of parts of the images to the viability score.

Figure 4:
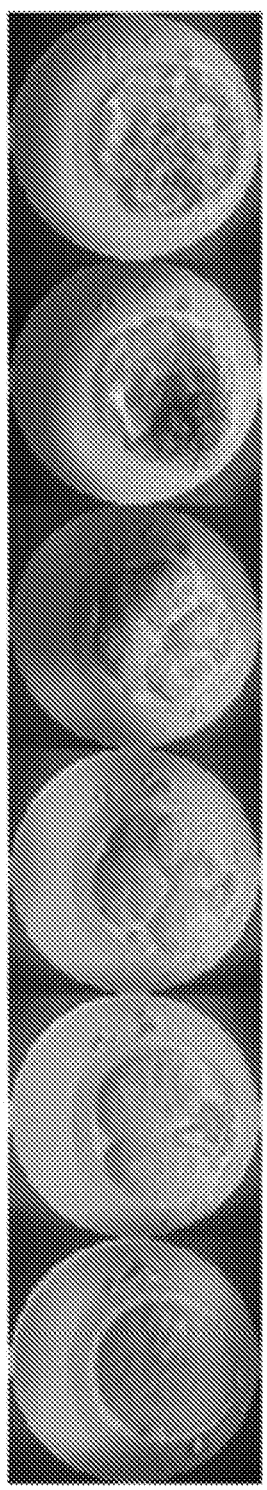
FIG. 4 shows one example of a heat map produced by the system.

In one example, the visual overlay is a heat map (also referred to as a contribution map), an example of which is shown in FIG. 4.

The heat map may be generated by analysing change of the viability score output by the deep learning model when occluding portions of the images in the time-lapse video data. For example, a 3D occlusion window can be applied to the video to occlude different portions of the video.

Figure 5A:
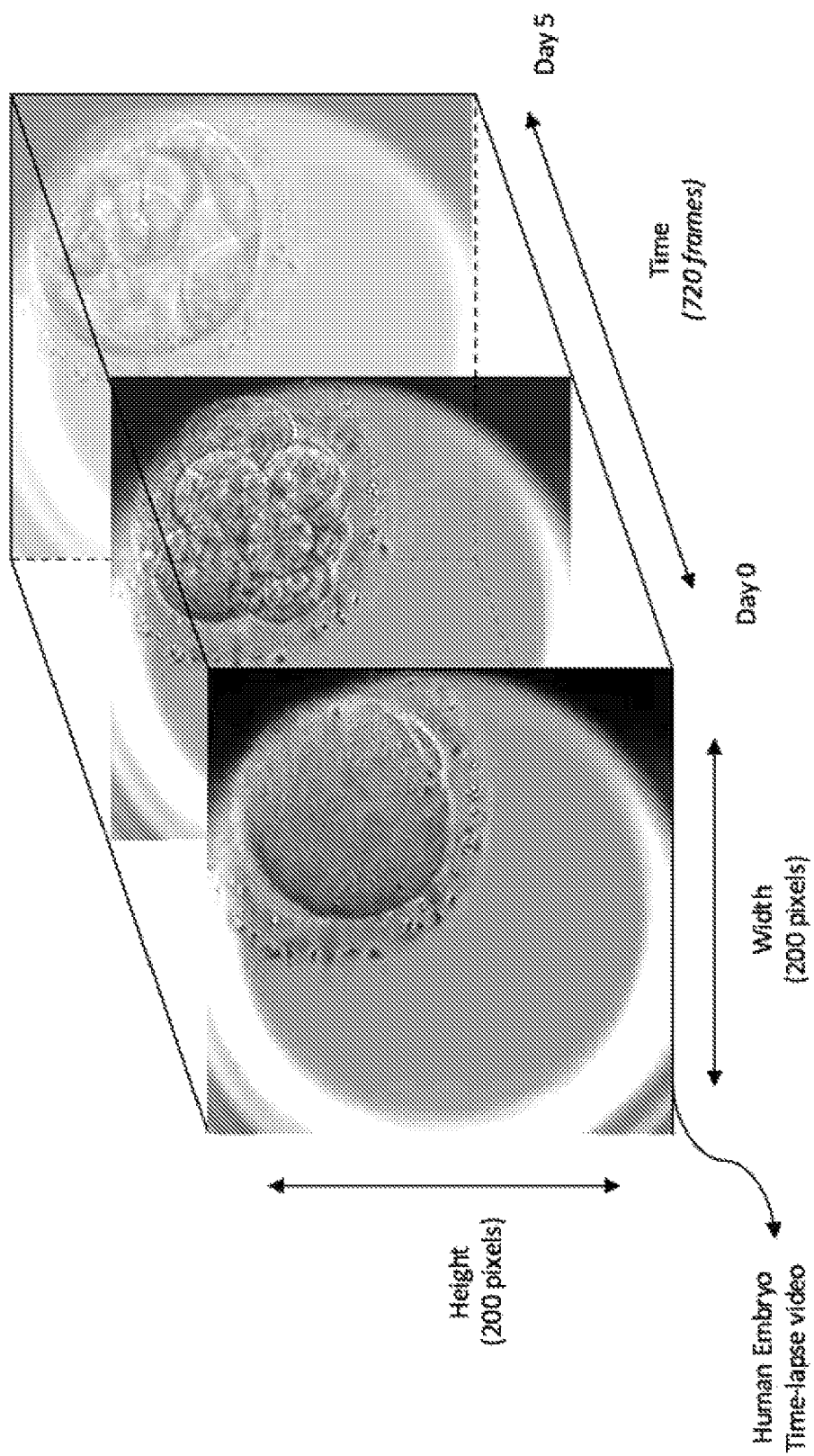
FIG. 5A shows an example of time-lapse video data.
Figure 5B:
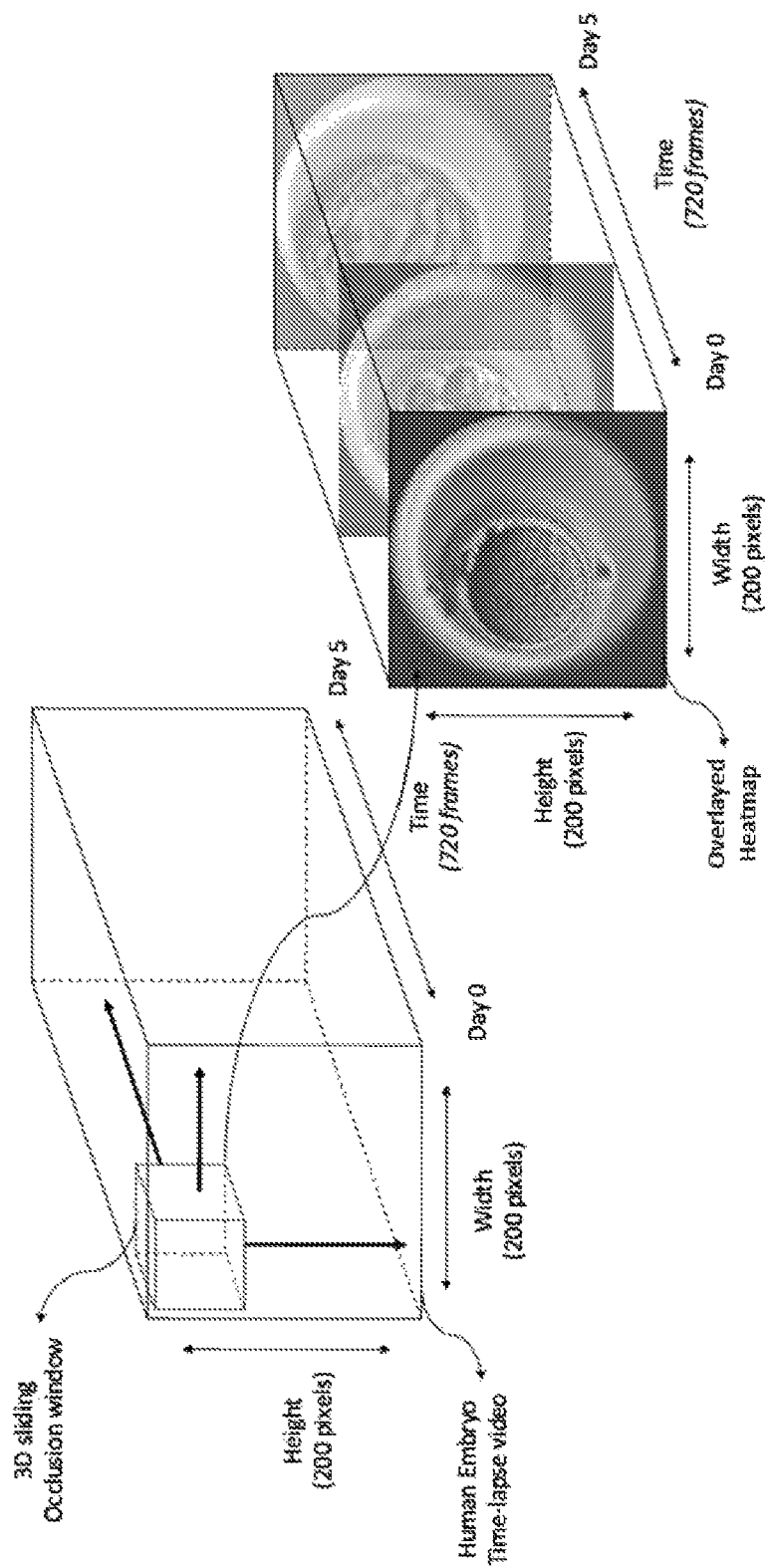
FIG. 5B illustrates application of a 3D occlusion window and heat maps generated for the time-lapse video data.

FIG. 5A shows an example of the time-lapse video data before adding the heat map. FIG. 5B illustrates the application of a 3D occlusion window and the generated heat map.

As shown in FIG. 5B, different intensities or colours may be used to represent levels of contribution toward embryo viability of each spatio-temporal region. For example, blue may indicate spatio-temporal regions that have low levels of contribution to the embryo viability (such a region may also be referred to as an "unfavourable spatio-temporal region"), while red may indicate spatio-temporal regions that have high levels of contribution to the embryo viability (such a region may also be referred to as a "favourable spatio-temporal region").

Figure 6:
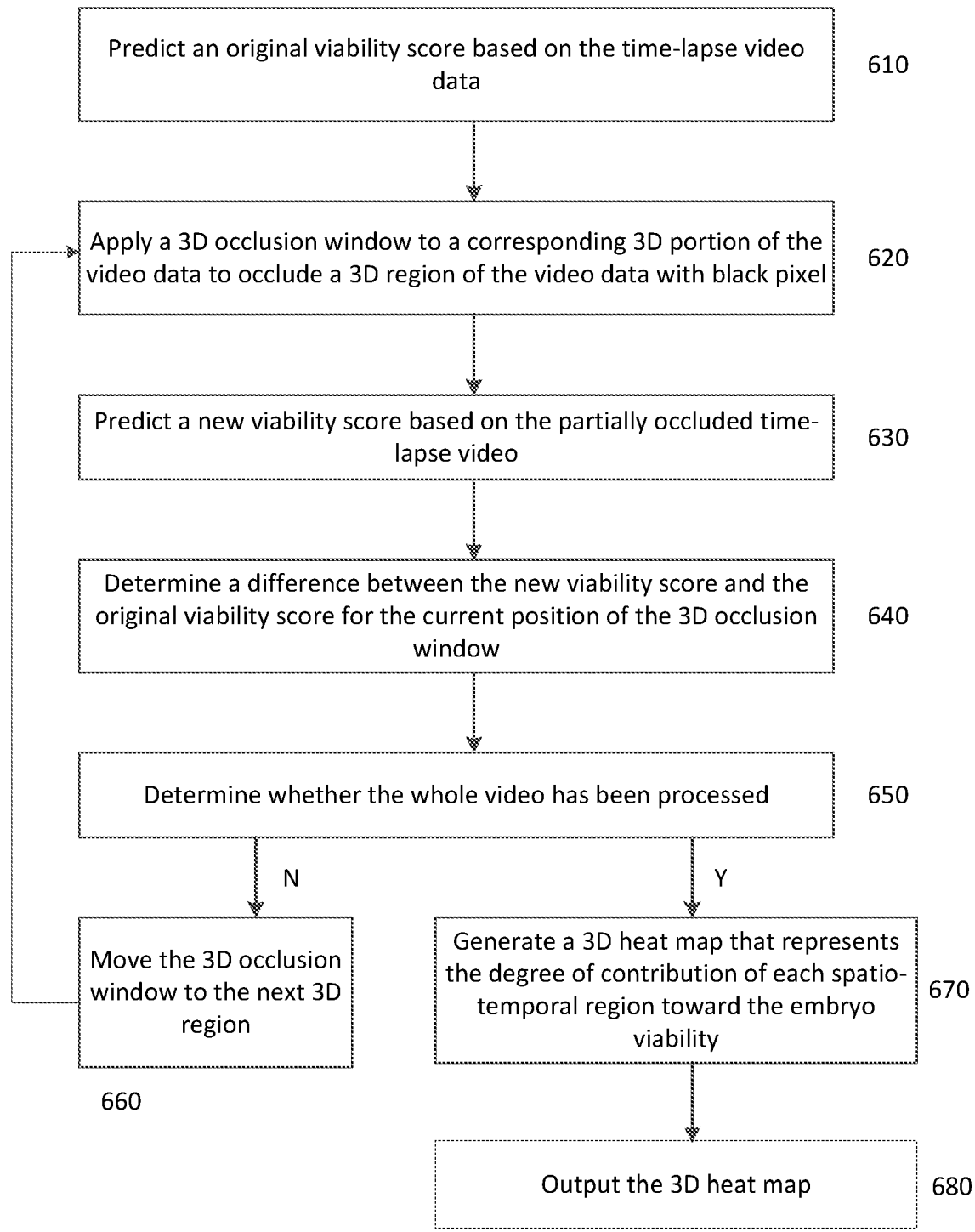
FIG. 6 shows method/processing steps for generating a heat map.

FIG. 6 illustrates an exemplary processing flow performed by the processor 108 in generating the heat map.

At Step 610, the processor 108 uses the 3D CNN model to predict an original viability score based on the time-lapse video data.

At Step 620, the processor 108 applies a 3D occlusion window to a corresponding 3D portion of the video data to occlude a 3D region of the video data with black pixel.

At Step 630, the processor 108 uses the same 3D CNN model to predict a new viability score based on the partially occluded time-lapse video.

At Step 640, the processor 108 determines a difference between the new viability score and the original viability score for the current position of the 3D occlusion window.

At Step 650, the processor 108 determines whether the whole video has been processed.

If not, the processor 108 moves the 3D occlusion window to the next 3D region at Step 660 and then loops back to Step 620.

If the whole video has been processed, the processor 108 proceeds to Step 670 to generate a 3D heat map that represents the degree of contribution of each spatio-temporal region toward the embryo viability.

Finally, at Step 680, the processor 108 outputs the generated 3D heat map.

The generated 3D heat map may be subsequently sent to a display device, such as the display 110, where the 3D heat map may be presented to human staff, e.g., an embryologist. This allows an embryologist to review and/or analyse the decision-making process of the machine learning model, and to learn the characteristics/features in the embryo video used by the machine learning model to assess the viability of the embryo. In this way, the heat map may improve the understanding of human medical professionals in embryo viability and help in diagnosing any abnormal behaviour by the system.

It will also be appreciated that the processor 108 as described herein may be integrated into other apparatuses and systems, such as, for example the incubator 102 used for storing and/or developing embryos prior to implantation. Accordingly, an incubator can incorporate a processing system, such as the processor 108 described herein. Alternatively, the processor 108 may be provided as an apparatus separate from the incubator 102, as shown in FIG. 1, e.g., in cloud servers.

Further, although in the example shown in FIG. 1 the processor 108 is in data communication with the incubator 102 and receives the time-lapse video data captured by the image sensor 106 directly from the incubator 102, in some embodiments, the time-lapse video data may be stored on a data store or a server which can be accessed or read by the processor 108 subsequently.

In some embodiments, the processor 108 may be communicably connected to the incubator 102 or the data store that stores the time-lapse video data via one or more wired and/or wireless networks. The determination of the viability of the embryo may be provided as web/cloud based service/application i.e., to be accessed via the Internet.

It will be appreciated that in addition to being embodied as a stand-alone system, or incorporated as part of another apparatus or system (e.g., incubator), embodiments of the present invention may include a method to be performed by a computer (or other suitable electronic processing device).

Figure 7:
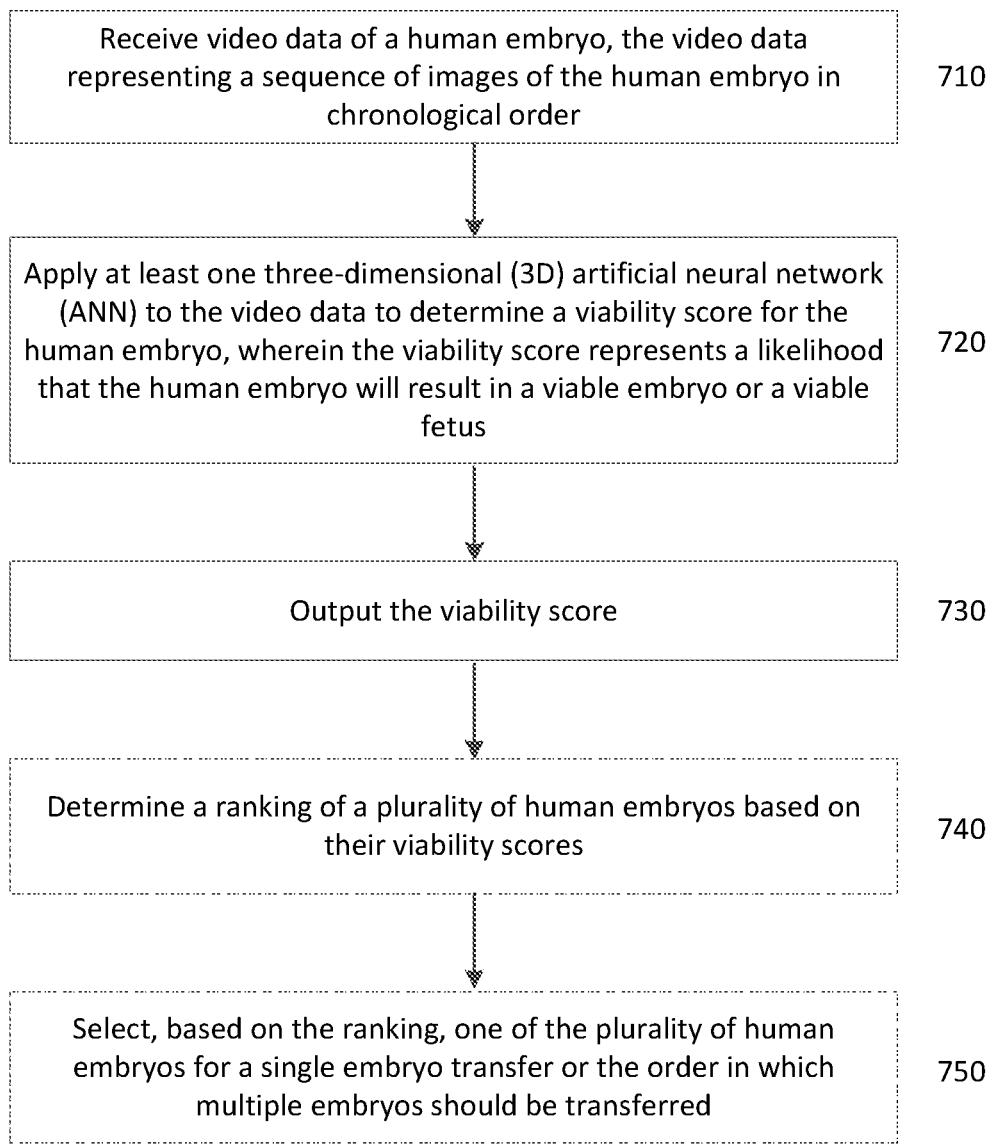
FIG. 7 shows method/processing steps for estimating embryo viability.

In such forms, embodiments provide a computer implemented method of estimating viability of human embryo for implantation. As shown in FIG. 7, the method includes the steps of:

receiving video data of a human embryo, the video data including a sequence of images of the human embryo in chronological order (Step 710);

applying at least one three-dimensional (3D) artificial neural network to the video data to determine a viability score for the human embryo, wherein the viability score represents a likelihood that the human embryo will generate an ongoing pregnancy (Step 720); and outputting the viability score (Step 730).

In some embodiments, the method may further include: determining a ranking of a plurality of human embryos based on their viability scores, as shown by Step 740 in FIG. 7.

In some embodiments, the method may further include: selecting, based on the ranking, one of the plurality of human embryos for a single embryo transfer or the order in which multiple embryos should be transferred, as shown by Step 750 in FIG. 7.

The selected embryos may be subsequently transferred into the uterus of a patient.

Also provided herein is a computer program including instructions that configure a computer to perform the method as described herein, which may be provided on a computer readable medium. In one example, the method is implemented on a remote server (e.g., cloud based server) to be accessed via a communication network (e.g., the internet).

Also provided herein is a method including:
generating a viability score for a human embryo by probabilistically classifying data representing a video of the human embryo with an artificial neural network (ANN); or
training an artificial neural network (ANN) to probabilistically classify data representing a video of a human embryo to generate a viability score for the human embryo.

Further provided herein is a system, including at least one processor configured to:
generate a viability score for a human embryo by probabilistically classifying data representing a video of the human embryo with an artificial neural network (ANN); or
train an artificial neural network (ANN) to probabilistically classify data representing a video of a human embryo to generate a viability score for the human embryo.

The presently described systems and methods may provide several advantages over conventional methods for estimating/predicting the viability of embryos.

For example, in implementing the system/method, human error may be reduced/removed the process of assessing the embryo quality. The system is objective and is not influenced by fatigue, emotional bias or inexperience. The viability score provided to each embryo is also reproducible and there is no variability between readers or labs.

The training of the deep learning model described herein do not require manual human labelling/annotation of embryo characteristics/features. The system/method described herein provides an end-to-end embryo assessment solution. As described hereinbefore, given that medical professionals currently do not have a comprehensive understanding of the characteristics/features suitable for assessing embryo quality, an end-to-end process can provide more accurate results than systems/methods that relying on manual selection/annotation of embryo characteristics/features. Furthermore the annotation and feature extraction step is very labour intensive typically take 5 to 10 minutes per embryo. Each treatment cycle can have up to 50 embryos.

The system/method may interpret time-lapse video much faster than a human embryologist. When implemented on a typical personal computer, the system/method can interpret about 10 embryos per 1 second. It is thus highly scalable for mass adoption. In some examples, the speed may be such to allow embryos to be interpreted almost instantly on demand, making patient scheduling more flexible.

The operational cost of implementing the system/method may be much cheaper than that of a highly trained embryologist. As a result, IVF laboratories can allocate their highly paid human resources toward other aspects of IVF.

In addition, the visual overlay, such as the heat map generated using the occluding window, allows embryologists to learn from the machine learning model. By using the heat map, the system/method described herein can empower embryologists and can be used as a tool for identifying unknown markers for embryo viability.

Example 1

A software tool/application for predicting pregnancy potential/viability of embryos by analysing time-lapse videos from incubators (e.g., Embryoscope®) was developed for implementation on a processing/computer system. The software implemented a deep learning model with 3D CNN networks.

A training dataset of embryo time lapse videos with known pregnancy outcomes was used to train the 3D CNN deep learning model. The training dataset included 903 time lapse videos, 657 with negative pregnancy outcomes and 246 with positive pregnancy outcomes. The videos were randomised into a training set (75%) and a testing set (25%) for post training validation.

Figure 8:
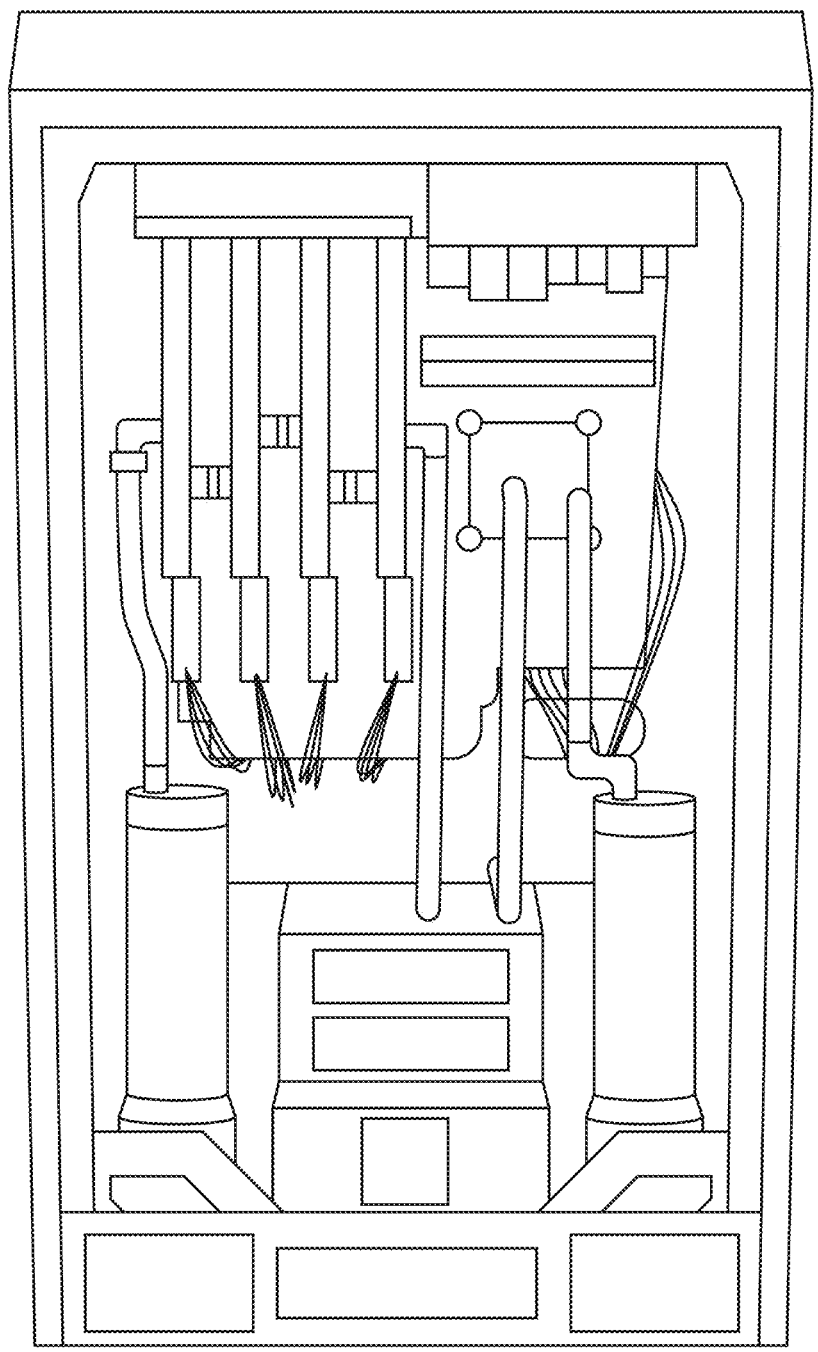
FIG. 8 shows an example of a computer for training the deep learning model.

The processing/computer system included a personal computer with four graphical processing units (GPUs) and 12 core central processing units (CPU), as shown in FIG. 8. The system was cooled by two separate water loops along with 12 high performance fans to prevent overheating.

Figure 9:
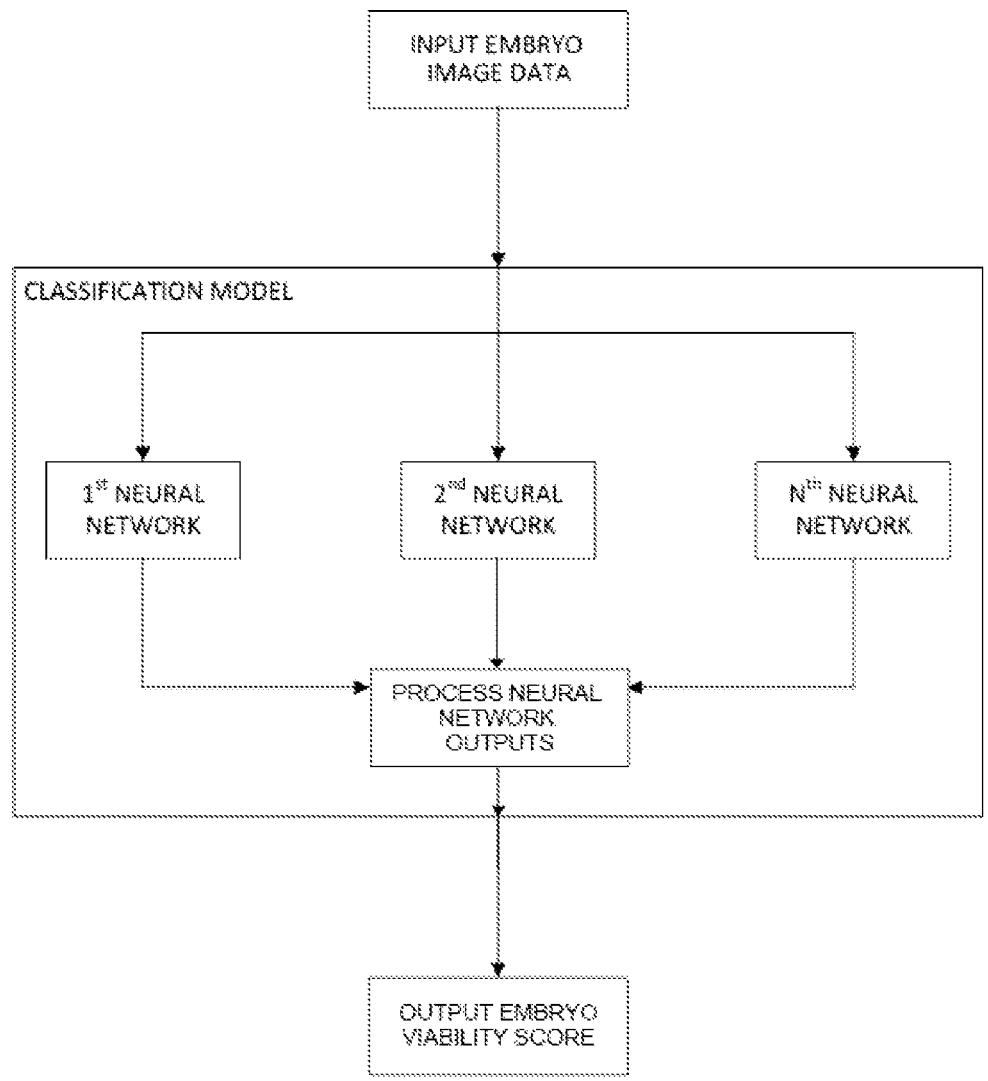
FIG. 9 illustrates ensembling of multiple neural networks according to one example.

As shown in FIG. 9, the 3D CNN deep learning model used in this example included three separate neural networks. To determine the viability score, each embryo time-lapse video was independently analysed by each of the three neural networks and the average of their predictions was reported as final output. The model returned a probability (viability) score that a given embryo will go on to create a clinical pregnancy (0%-100%).

Figure 10:
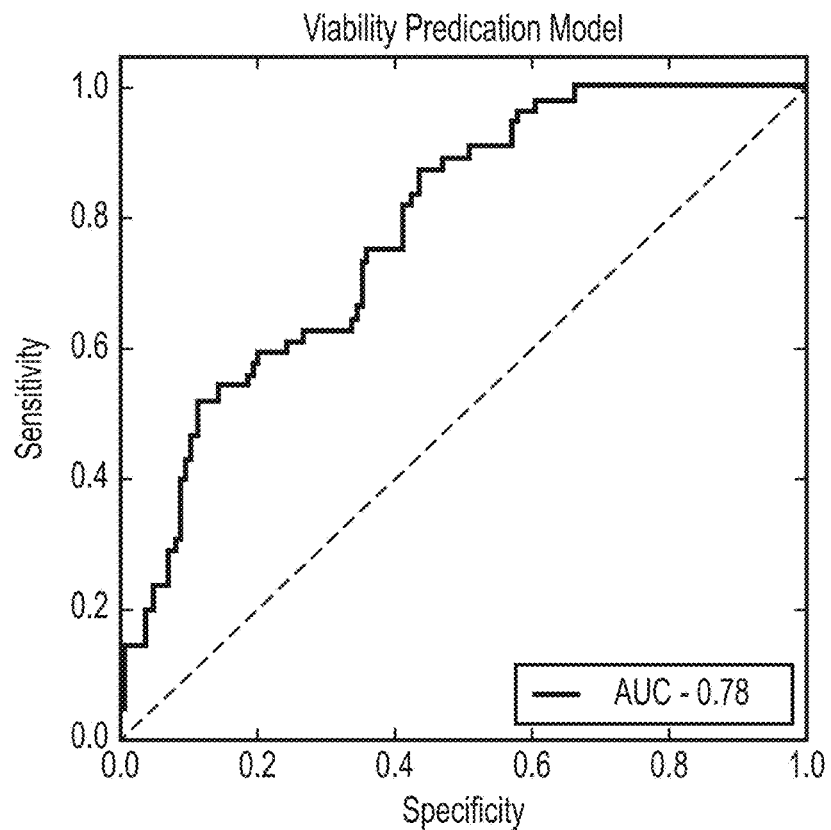
FIG. 10 is a graph showing performance of the deep learning model according to one example.

After the training process, the model scored 180 of the embryos from the testing set. As shown in FIG. 10, the deep learning model achieved an area under the curve (AUC) of 0.78, out-performing human graders (AUC=0.55-0.75). At a cut-off threshold of 20%, the model had a sensitivity of 95%, specificity of 43%, positive likelihood ratio of 1.65 and negative likelihood ratio of 0.13.

Figure 11:
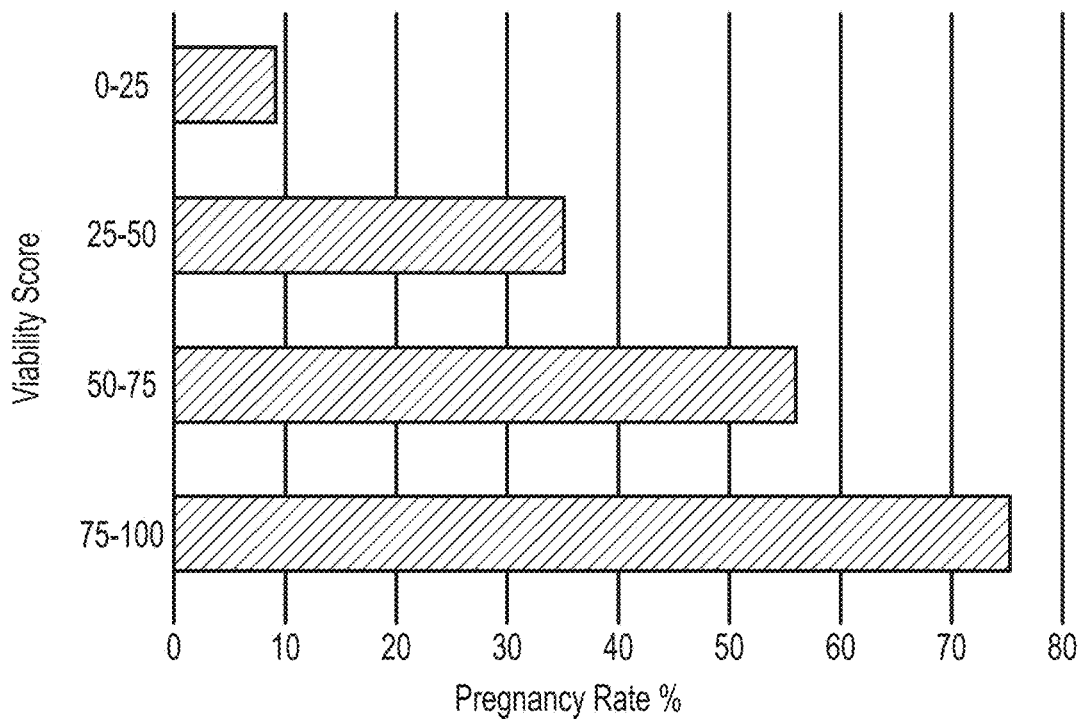
FIG. 11 is a graph showing an exemplary correlation between output viability score and actual pregnancy outcome.

The returned viability score was also well correlated to the actual pregnancy rate. FIG. 11 shows the pregnancy rate of embryos when compared to viability score produced for those embryos. It is shown that the model could clearly discriminate embryos with high pregnancy potential vs. low pregnancy potential. In addition, its predicted probability of pregnancy was very similar to the actual pregnancy rate.

The software tool allowed a user to overlay a heat map (as shown in FIG. 4) that highlighted the point in time (i.e., during embryo development) as well as the location in space (i.e., part of video image) that contributed the most to the prediction provided by the model. The heat map provided an insight to embryologists about the model's decision making process. This heat map along with the viability score could be a part of the patient's treatment record.

In this particular example, the input format was any time-lapse video (e.g., .avi file) exported from the Embryo-Scope® software including ICSI or IVF embryos. It will be appreciated that the videos could have different starting times in the embryo development cycle (e.g., D5-D6 Blastocyst stage, D2-3 Cleavage stage).

Figure 12:
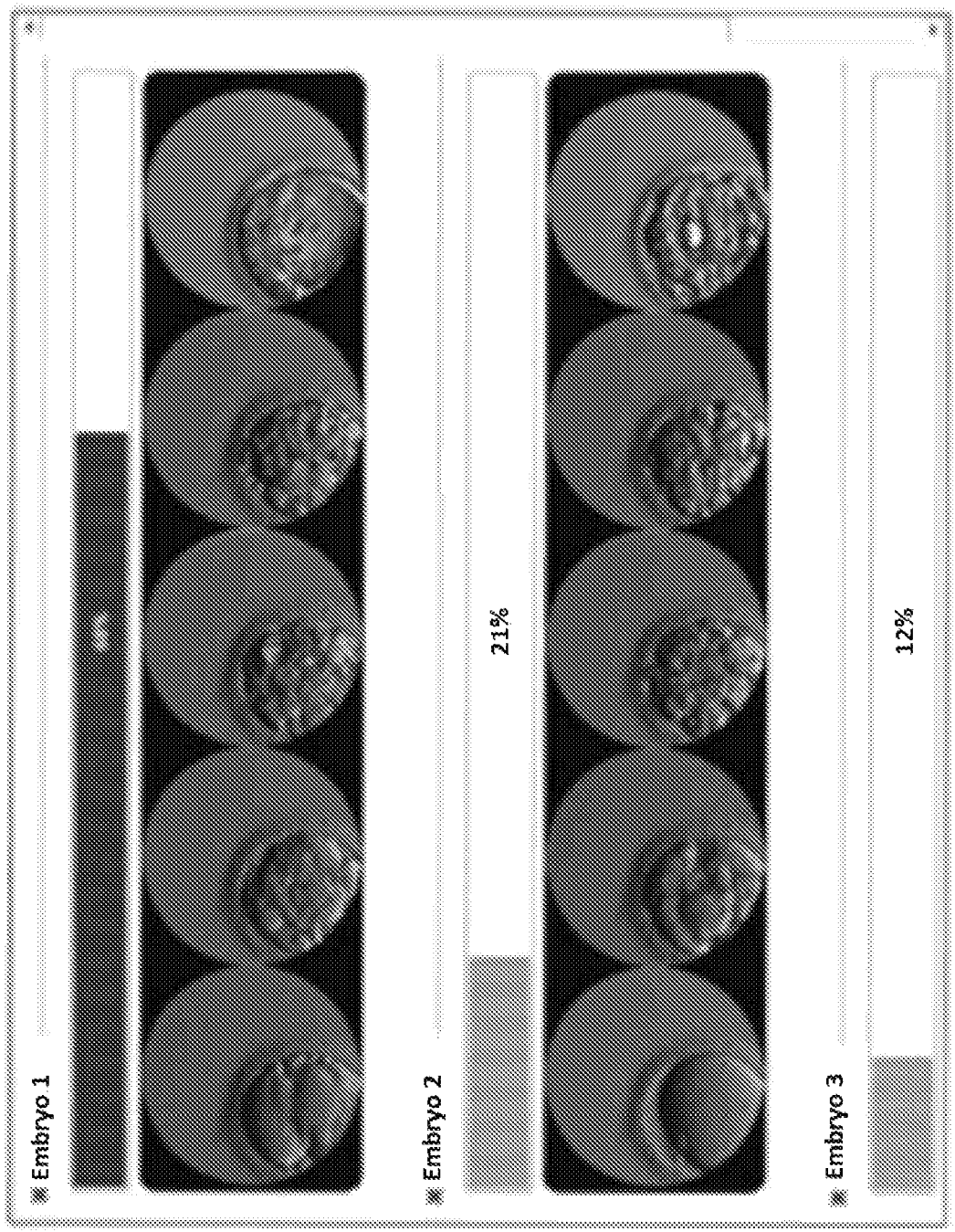
FIG. 12 is one example of a software interface of the system.

Multiple embryos/videos may be assessed simultaneously. In such instances, the software/system ranked the embryos in accordance with their viability score and the embryo with the highest score will be recommended for a single embryo transfer. In the example shown FIG. 12, "Embryo 1" was the recommended embryo. The remainder of the embryos could then be frozen, and subsequently transferred in descending order of viability score, so as to give the patient the highest chance of a successful pregnancy outcome. Furthermore, a specific cut-off threshold could be decided by each IVF clinic, and any embryo scoring less than this threshold could be deemed as "non-viable" and not be considered for freezing or embryo transfer.

Figure 13:
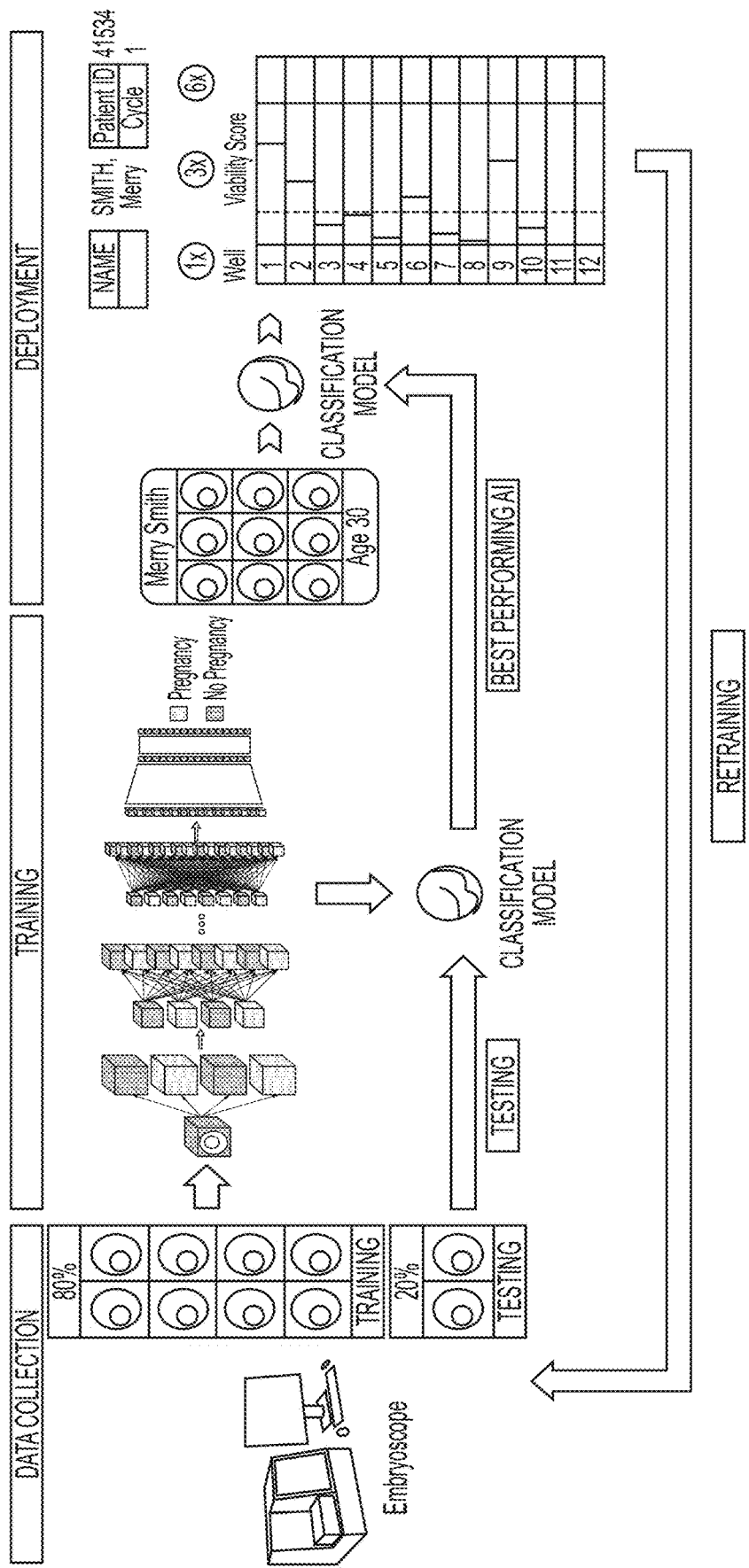
FIG. 13 is a schematic overview of one example of implementation/training of a classification model for the systems/methods.

In this example, the software tool/application ran on the Linux operating system. It will be appreciated that other versions may readily be produced to operate on different operating systems. It will be appreciated that the software/system may be deployed as web/cloud based service/application, i.e., to be accessed via the Internet. It will be appreciated that the model may be improved by adding more data into the training process. FIG. 13 shows an overview of one example of training, implementation and retraining of the deep learning model.

Example 2

A software tool/application for predicting pregnancy potential/viability of embryos by analysing time-lapse videos from incubators (e.g., Embryoscope® or EmbryoScope+®) was developed for implementation on a processing/computer system. The software implemented a deep learning model included a 3D CNN as shown in FIGS. 3A and 3B.

Data Collection

Time-lapse videos of embryo exported from commercially available time-lapse incubators such as EmbryoScope® or EmbryoScope+® was collected from IVF laboratory and used to train the deep learning model.

Figure 15:
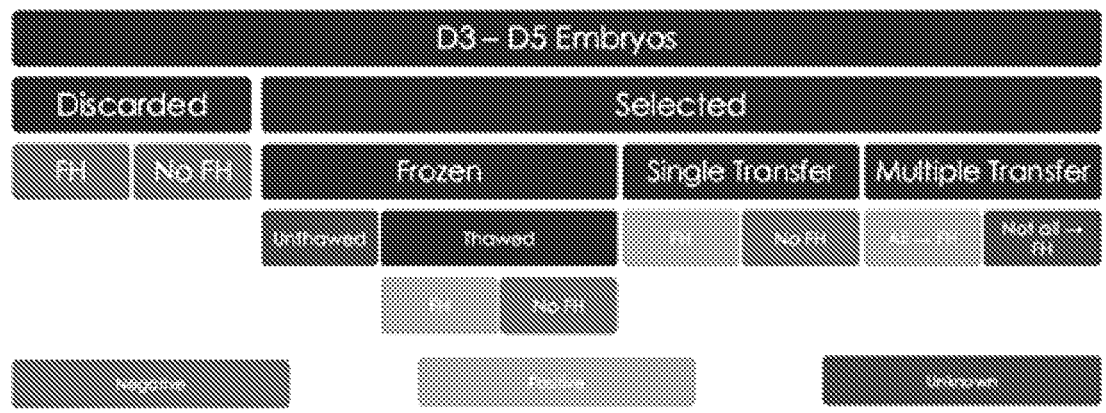
FIG. 15 shows the labelling of the time-lapse videos used for training the deep learning model.

The outcome of each embryo was obtained from a patient management system and was used to label these time-lapse videos using the schematic shown in FIG. 15.

In particular, embryos that were transferred to the patient and resulted in a fetal heart detectable on antenatal ultrasound at 6 weeks post-embryo transfer were labelled "1" for positive. Embryos that were either discarded by embryologist or did not result in a fetal heart were labelled "0" for negative. All embryos with unknown or undetermined outcome were not used for training.

Data Splitting

Time-lapse videos of embryo exported from commercially available time-lapse incubators such as EmbryoScope® or EmbryoScope+® were collected from IVF laboratory and used to train the deep learning model.

In total, the full dataset included 1281 time lapse videos.

Figure 16:
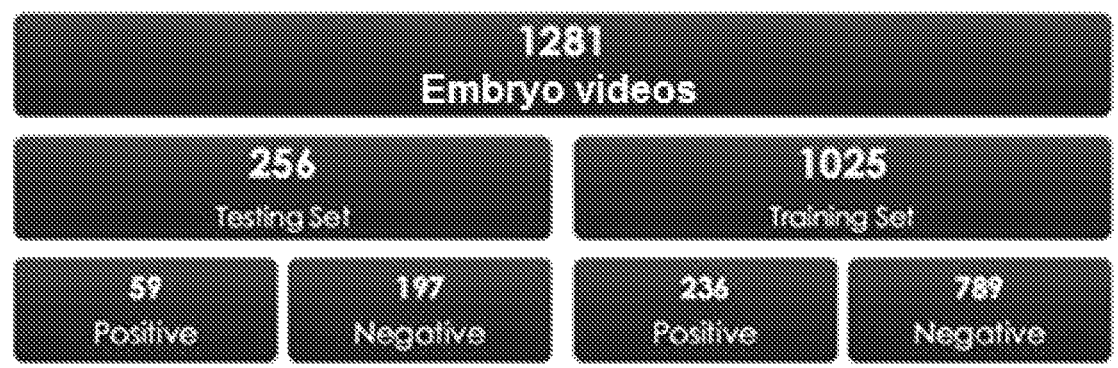
FIG. 16 shows the split of a full dataset into a training set and a testing set.

As shown in FIG. 16, the full dataset was randomly split into a training set (80%) and a testing set (20%) The neural network was trained on the training set only. Once the training was completed, the model was tested on the testing set to obtain performance characteristic metrics.

The training set included 1025 time lapse videos, 789 with negative pregnancy outcomes and 236 with positive pregnancy outcomes. The testing set included 256 time lapse videos, 197 with negative pregnancy outcomes and 59 with positive pregnancy outcomes.

Data Preparation for Training

The time-lapse videos in the training dataset were pre-processed before being used for training the deep learning model. Firstly, the time-lapse videos were standardised in time to ensure that all embryo videos span 5 days. A circular cropping function was then applied to each video to centre the embryo and to block out unwanted areas, enabling the neural network to focus its learning toward the embryo. Contrast limited adaptive histogram equalisation (CLAHE) was then applied to all images in the embryos videos to enhance the image quality. Finally, all embryo videos were resized to a fixed shape of 128×128×128×1 (128 frames of 128×128 pixels and 1 channel of black and white).

FIGS. 17A and 17B show an example of images at slightly different points in time in a time-lapse embryo video before and after the pre-processing, respectively.

Data Augmentation

In order to increase the size of the original dataset, various transformations were randomly applied to each time-lapse video to create new videos that were visually different to the original video. This allows the neural network to generalise better to unseen examples, thereby further improving the performance of the neural network.

These augmentation methods included:
Random 360-degree rotation;
Random horizontal and vertical flip;
Random re-scaling of the video size (1.2×-0.8×);
Random playback speed adjustment (1.2×-0.8×);
Gaussian blur to mimic out of focus effect; and
Randomly blacking out portions of the video.

During each step of the training process, a batch of video was randomly selected from the dataset and the random set of augmentation operations were applied to this batch to create slightly different set of videos for training. This process was repeated as the entire dataset was looped over multiple times.

Training of the Deep Learning Model

A 3D CNN deep learning model as shown in FIGS. 3A and 3B was used in this example.

The 3D CNN was trained with the time-lapse video dataset using stochastic gradient decent method. The loss function used for training was categorical cross-entropy. The CNN was trained using a learning rate of 0.00001 and momentum of 0.9 for 102,400 steps. The learning rate was then lowered to 0.000001 and the network was trained for a further 102,400 steps.

The training was performed using a personal computer with four graphical processing units (GPUs), such as NVIDIA 1080 Ti, 6 core central processing units (CPUs), such as Intel i7-6850K, and a 64 Gb RAM.

Ensembling Models

In this example, multiple 3D CNNs were ensembled to further improve the performance of the CNN.

The ensembling method of choice was 5-fold cross-validation and model bagging. As shown in FIG. 18, the full dataset was divided into five equal parts. One of these parts was sequentially held out for testing and the model was trained using the other 4 parts. The end results were 5 unique neural networks that were trained on slightly different datasets and carried different biases. When making a prediction on a new embryo, all 5 neural networks were used to score the embryo independently, and their scores were averaged to obtain the final score. This resulted in a unifying model that was more robust than any individual model alone.

Deployment Software

A software package was developed to apply the neural network to new time-lapse videos. The software was configured to accept a video file of the time-lapse sequence and output a viability score (which may also referred to as an "EB.Score") for each embryo. The viability score represented the likelihood that the given embryo would lead to a fetal heart on ultrasound 6 weeks after that embryo was transferred.

The human embryologist could subsequently make a decision on the best embryo to be transferred based on the viability score.

Figure 19:
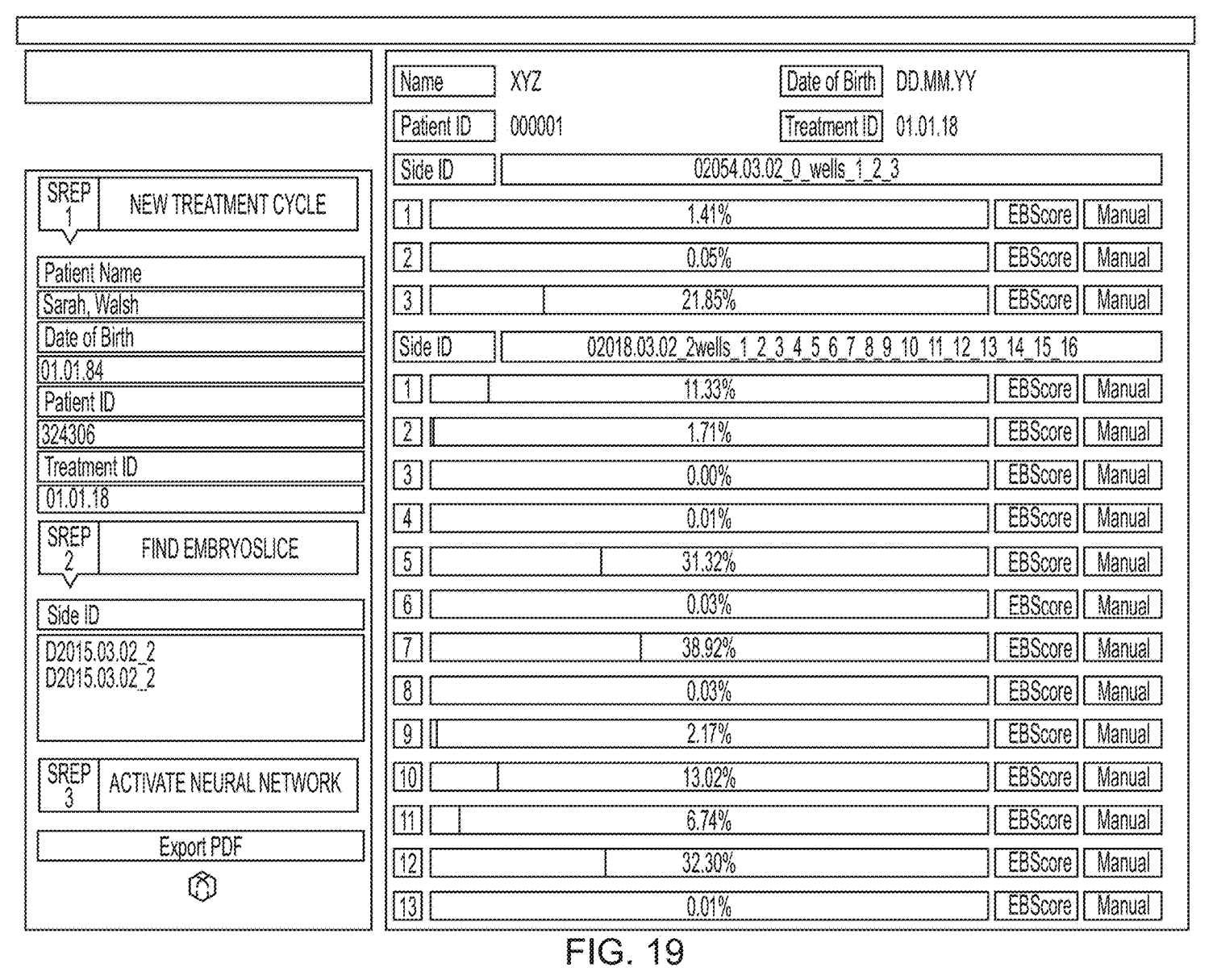

FIG. 19 illustrates an exemplary user interface of the software package that displays the viability score (in the form of a percentage) generated for a number of embryos. The software package may be deployed on a suitable computer device, such as a laptop used in IVF labs. As shown, the green bar (or light grey) represents the embryo with the highest viability score (38.92%), the blue bars (or dark grey) represent embryos that have acceptable viability scores, and the white bars represent embryos that have low viability scores (i.e., nonviable embryos).

Alternatively, the method may be implemented by any other suitable computing device, or provided as a web-based or cloud-based service that can be accessed via a network such as the Internet.

It will also be appreciated that the deep learning model may be improved by adding more data into the training process. In other words, the deep learning model is a self-improving and self-tuning model. The performance and robustness of the model can be further improved over time by retraining the CNN, while more embryos are accessed by the deep learning model.

Generating the Heat Map

In order to provide a visual representation of which areas of the video resulted in a significant change in the returned viability score, heat maps were generated by sequentially occluding parts of the video and repeating the scoring process.

A heat map generated for an embryo video indicated areas of the video where the CNN was paying close attention to in making its final decision.

Figure 14:
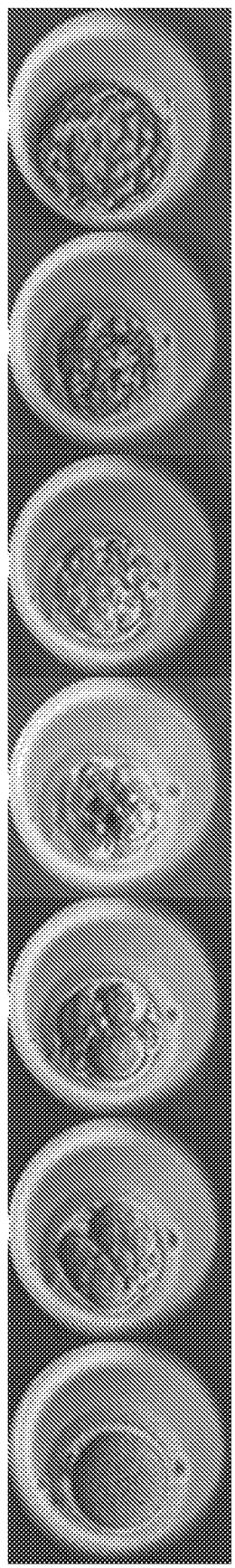
FIG. 14 shows another example of the heat map.

FIG. 14 shows examples of the heat map generated, in which blue regions (in the central area of the fourth and fifth image from the left) represent regions that have low levels of contribution to the embryo viability (such a region may also be referred to as an "unfavourable region"), while red regions (in the central cell area of the sixth and seventh images from the left) represent regions that have high levels of contribution to the embryo viability (such a region may also be referred to as a "favourable region").

The heat map allowed the neural network to communicate its decision making process in a humanly readable way, thus improves the collaboration between the neural network and human embryologists.

Interpretation

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Many modifications will be apparent to those skilled in the art without departing from the scope of the present invention.

The invention claimed is:

1. A computer-implemented method, including the steps of:
   receiving video data of a human embryo, the video data captured by an image sensor of an incubator and including a sequence of images of the human embryo in chronological order, the video data including spatial dimensions and temporal dimensions;
   applying at least one three-dimensional (3D) artificial neural network (ANN) including a 3D convolutional neural network (CNN) to the video data to determine a viability score for the human embryo, wherein the viability score represents a likelihood that the human embryo will result in a viable embryo or a viable fetus, the 3D convolutional neural network (CNN) being configured to extract features from both the spatial dimensions and the temporal dimensions of the video data by performing 3D convolutions, and the 3D CNN including a plurality of convolution layers each using a 3D convolution kernel, and a plurality of pooling layers each using a 3D pooling kernel that determine the viability score; and
   outputting the viability score.

2. The method of claim 1, wherein the viability score represents a probability that transferring the human embryo will result in a viable fetus.

3. The method of claim 1, wherein the viability score represents a probability that transferring the human embryo will result in any one or more of the following:
   a viable fetal heart detected within a predetermined period of time after embryo transfer;
   a biochemical pregnancy detected based on a urine test or a blood test;
   a viable gestational sac or a viable yolk sac detected on ultrasound at a predetermined time after embryo transfer; and
   a live birth at the end of pregnancy.

4. The method of claim 1, wherein the 3D ANN is trained by using:
   video data representing a plurality of sequences of images of a plurality of human embryos; and
   pregnancy outcome data that indicates whether each of the plurality of human embryos has resulted in a viable embryo or a viable fetus.

5. The method of claim 4, wherein the training of the 3D ANN is performed without manual selection or extraction of features, or human annotation of key development events.

6. The method of claim 1, further including one or more of:
   standardising the received video data so that all videos span a predetermined time period;
   cropping the video data to retain predetermined areas of the data;
   adjusting contrast of the images in the video data; and
   resizing the images in the video data to a predetermined image size.

7. The method of claim 1, further including:
   processing the video data by adding a visual overlay to at least some images of the video data, the visual overlay indicative of contributions of respective portions of the images to the viability score; and
   outputting the images with the visual overlays.

8. The method of claim 7, wherein the visual overlay is a heat map.

9. The method of claim 7, wherein the visual overlay is generated by:
   determining changes of the viability score output caused by occluding portions of the images or sequence of images in the video data.

10. The method of claim 9, wherein occluding portions of the images in the video data includes applying a three-dimensional occlusion window to the video data.

11. The method of claim 1, further including:
determining a ranking of a plurality of human embryos based on their viability scores.

12. The method of claim 11, further including:
selecting, based on the ranking, one of the plurality of human embryos for a single embryo transfer or the order in which multiple embryos should be transferred.

13. A system, including at least one processer configured to:
receive video data of a human embryo, the video data captured by an image sensor of an incubator and including a sequence of images of the human embryo in chronological order, the video data including spatial dimensions and temporal dimensions;
apply at least one three-dimensional (3D) artificial neural network (ANN) including 3D convolution neural network (CNN) to the video data to determine a viability score for the human embryo, wherein the viability score represents a likelihood that the human embryo will result in a viable embryo or a viable fetus, the 3D convolutional neural network (CNN) being configured to extract features from both the spatial dimensions and the temporal dimensions of the video data by performing 3D convolutions, and the 3D CNN including a plurality of convolution layers each using a 3D convolution kernel, and a plurality of pooling layers each using a 3D pooling kernel that determine the viability score; and
output the viability score.

14. The system of claim 13, wherein the system includes:
an image sensor for capturing video data of the human embryo;
wherein the processor is configured to receive the captured video data from the image sensor.

15. The system of claim 13, wherein the system includes a time-lapse incubator.

16. A method including:
generating a viability score for a human embryo by probabilistically classifying data including spatial dimensions and temporal dimensions and representing a video of the human embryo with a three-dimensional (3D) artificial neural network (ANN),
wherein the 3D artificial neural network is a 3D convolutional neural network (CNN), and
wherein the 3D convolutional neural network (CNN) being configured to extract features from both the spatial dimensions and the temporal dimensions of the video data by performing 3D convolutions, and the 3D CNN includes a plurality of convolution layers each using a 3D convolution kernel, and a plurality of pooling layers each using a 3D pooling kernel that determine the viability score; or
training a three-dimensional (3D) artificial neural network (ANN) to probabilistically classify data including spatial dimensions and temporal dimensions and representing a video of a human embryo to generate a viability score for the human embryo,
wherein the 3D artificial neural network is a 3D convolutional neural network (CNN) configured to extract features from both the spatial and the temporal dimensions of the data representing the video by performing 3D convolutions, and
wherein the 3D CNN includes a plurality of convolution layers each using a 3D convolution kernel, and a plurality of pooling layers each using a 3D pooling kernel that determine the viability score.

17. The method of claim 16, wherein the viability score represents a likelihood that the human embryo will result in a viable embryo or a viable foetus.

18. The method of claim 16, wherein the video is of the human embryo in an incubator optionally for a preselected period of time; and/or wherein the video includes a series of images optionally including time-lapse images.

19. The method of claim 16, wherein the ANN is trained using:
data representing a plurality of videos of human embryos; and
data representing whether the human embryos have resulted in respective viable embryos or viable fetuses.

20. A system, including at least one processor configured to:
generate a viability score for a human embryo by probabilistically classifying data representing a video of the human embryo with a three-dimensional (3D) artificial neural network (ANN),
wherein the 3D artificial neural network is a 3D convolutional neural network (CNN) configured to extract features from both the spatial and the temporal dimensions of the data by performing 3D convolutions, and
wherein the 3D CNN includes a plurality of convolution layers each using a 3D convolution kernel, and a plurality of pooling layers each using a 3D pooling kernel; or
train a three-dimensional (3D) artificial neural network (ANN) to probabilistically classify data representing a video of a human embryo to generate a viability score for the human embryo,
wherein the 3D artificial neural network is a 3D convolutional neural network (CNN) configured to extract features from both the spatial and the temporal dimensions of the data by performing 3D convolutions, and
wherein the 3D CNN includes a plurality of convolution layers each using a 3D convolution kernel, and a plurality of pooling layers each using a 3D pooling kernel that determine the viability score.

* * * * *